(12) United States Patent
Spens et al.

(10) Patent No.: US 10,603,464 B2
(45) Date of Patent: Mar. 31, 2020

(54) STERILE BARRIER PRODUCT PACKAGING

(71) Applicant: Medtronic Vascular, Inc., Santa Rosa, CA (US)

(72) Inventors: Courtney Spens, Santa Rosa, CA (US); Jeffrey Barnell, Santa Rosa, CA (US); James R. Keogh, Maplewood, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2 days.

(21) Appl. No.: 15/838,549

(22) Filed: Dec. 12, 2017

(65) Prior Publication Data

US 2019/0175868 A1 Jun. 13, 2019

(51) Int. Cl.
| | | |
|---|---|---|
| *A61M 25/00* | (2006.01) | |
| *B65D 1/34* | (2006.01) | |
| *A61B 50/33* | (2016.01) | |
| *B65D 43/16* | (2006.01) | |
| *B65D 51/24* | (2006.01) | |
| *B65D 51/28* | (2006.01) | |
| *A61L 2/26* | (2006.01) | |
| *A61B 50/30* | (2016.01) | |
| *A61B 50/00* | (2016.01) | |
| *A61L 2/20* | (2006.01) | |

(52) U.S. Cl.
CPC .......... *A61M 25/002* (2013.01); *A61B 50/30* (2016.02); *A61B 50/33* (2016.02); *A61L 2/26* (2013.01); *B65D 1/34* (2013.01); *B65D 43/16* (2013.01); *B65D 43/162* (2013.01); *B65D 51/245* (2013.01); *B65D 51/28* (2013.01); *A61B 2050/005* (2016.02); *A61B 2050/0056* (2016.02); *A61B 2050/0066* (2016.02); *A61B 2050/0067* (2016.02); *A61B 2050/3008* (2016.02); *A61L 2/206* (2013.01); *A61L 2202/12* (2013.01); *A61L 2202/181* (2013.01); *A61L 2202/182* (2013.01); *A61L 2202/24* (2013.01)

(58) Field of Classification Search
CPC ...... A61M 25/002; A61B 50/33; A61B 50/30; A61B 2050/3015; A61B 50/00; A61B 2050/0065; A61B 2050/005; B65D 1/34; B65D 2203/02; B65D 43/16
USPC ......................................... 206/438, 363, 439
See application file for complete search history.

(56) References Cited

U.S. PATENT DOCUMENTS

RE27,519 E * 10/1972 Shepherd ............... A61B 50/30
 206/363
5,495,944 A * 3/1996 Lermer .............. B65D 23/0842
 206/459.1

(Continued)

*Primary Examiner* — Steven A. Reynolds
(74) *Attorney, Agent, or Firm* — Dicke, Billig & Czaja, PLLC

(57) ABSTRACT

Aspects of the disclosure relate to packaging assemblies including a tray having at least one compartment adapted to receive a medical device component or product. The packaging assemblies a barrier film covering the compartment and a lid pivotally attached to the tray; wherein the tray and the lid each include cooperative latching features. The lid defines a recess in which one or more product items can be stored and the packaging assembly further includes a label removably secured over the recess and the sheet of product documentation. Methods of assembling, sterilizing and opening such packaging assemblies are also disclosed.

16 Claims, 8 Drawing Sheets

(56) References Cited

U.S. PATENT DOCUMENTS

| | | | | |
|---|---|---|---|---|
| 6,036,021 A * | 3/2000 | Moi | ................ | B65D 43/162 |
| | | | | 204/456 |
| 6,907,992 B2 * | 6/2005 | McMichael | ............ | A61B 50/30 |
| | | | | 206/370 |
| 8,056,719 B2 * | 11/2011 | Porret | ................ | A61L 2/26 |
| | | | | 206/370 |
| 9,744,333 B2 * | 8/2017 | Terzibashian | ........ | A61M 25/002 |
| 2003/0183540 A1 * | 10/2003 | Onishi | ................ | B65D 43/168 |
| | | | | 206/205 |
| 2008/0160143 A1 * | 7/2008 | Edwards | ................ | B65D 1/34 |
| | | | | 426/129 |
| 2011/0248033 A1 * | 10/2011 | Mehrvijeh | ............ | B65D 43/02 |
| | | | | 220/254.3 |
| 2013/0105344 A1 * | 5/2013 | Hartley | ............. | A61B 1/00062 |
| | | | | 206/363 |
| 2015/0197387 A1 * | 7/2015 | Yeager | ................ | B65D 81/20 |
| | | | | 206/499 |

* cited by examiner

STERILE BARRIER PRODUCT PACKAGING

BACKGROUND

Many medical devices components, particularly those used with catheter-based delivery systems and perfusion products, are packaged in pouches or lidded trays that are terminally sterilized prior to use. Such medical device components are often delicate, complex and require careful handling to prevent damage to the components and also maintain sterile barrier features. Some known packages include a pouch in which the medical device component is packaged for delivery and storage. Lidded trays often provide superior sterile barrier performance as compared to pouches, however, known lidded trays typically also require a shelf carton to protect the lidded tray during distribution and also to retain other included product documentation, such as instructions for use. Such shelf cartons increase the footprint of the package and generate an increase in package volume, which increases shipping costs significantly as many shipping providers charge disproportionally larger fees for shipping packages that have a low geometric density. Lidded trays shipped in a shelf carton also require two sets of labels, one for the tray and one for the carton, which further increases the cost and complexity of the packaging.

The present disclosure addresses problems and limitations associated with the related art.

SUMMARY

The present inventors have identified that there are challenges to packaging medical device components and products with laminating film to provide a sterile barrier pouch. Such film sometimes fails due to abrasion and film delamination caused by the interaction of the component and the pouch in which it is contained. This can be especially true for devices that have significant three-dimensional volume and/or include protrusions or sharp edges, such and components often used in catheter based delivery systems and perfusion products. Retesting and recertification of products and components packaged in damaged packaging is expensive and resource intensive.

Aspects of the disclosure relate generally to packaging assemblies for medical device components. In particular, various disclosed embodiments are further particularly useful for packaging medical device components/products that may have significant three-dimensional volume and/or protrusions or sharp edges while maintaining the size of the packaging assembly relatively small. The medical device or component to be stored within the compartment can be considered part of the packaging assembly in some embodiments or a separate component to be used with the packaging assembly in other embodiments.

Aspects of the disclosure further relate to methods including packaging, sterilizing and opening packaging assemblies. Such methods can include providing a packaging assembly including a tray including at least one compartment. A medical device component is positioned within the compartment and a barrier film is positioned to cover the compartment. In some embodiments, the barrier film is made of flashspun high-density polyethylene fibers to allow for the egress of various gas sterilization techniques. Therefore, at this stage, the medical device component can be sterilized, while sealed in the compartment and under the permeable barrier film. The packaging assembly further includes a lid that can be selectively positioned over the compartment of the tray. The tray and the lid each include cooperative latching features and the lid defines a recess in which product items be stored. In some embodiments, sterilization of the medical device component is conducted before the lid is closed or secured over the barrier film. In other embodiments, the packaging is sterilized while the lid is positioned over the tray and barrier film. In such methods, the lid can include vents extending through the lid and to the barrier film. Covering the recess is a label that can optionally seal a portion of the lid to the tray. Prior to opening the lid, the label can be broken adjacent the tray, which serves as an indication that the packaging assembly has been opened. Once the label is broken and removed, the product items are accessible for removal or can remain stored with the product packaging until needed.

Various packaging assemblies described in this disclosure are configured to support and protect the medical device component or product during transit and storage, while also providing a significantly smaller footprint than traditional packaging arrangements. The disclosed packaging arrangements are also expected to require less pieces/materials, reduce inventory and shipping costs, provide a superior sterile barrier, protect the barrier from damage during transportation and handling, manage product items or accessories and provide better visibility of the stored component as compared to many conventional sterile medical device component packages. Other benefits will become apparent in view of this disclosure.

DETAILED DESCRIPTION

Figure 1:
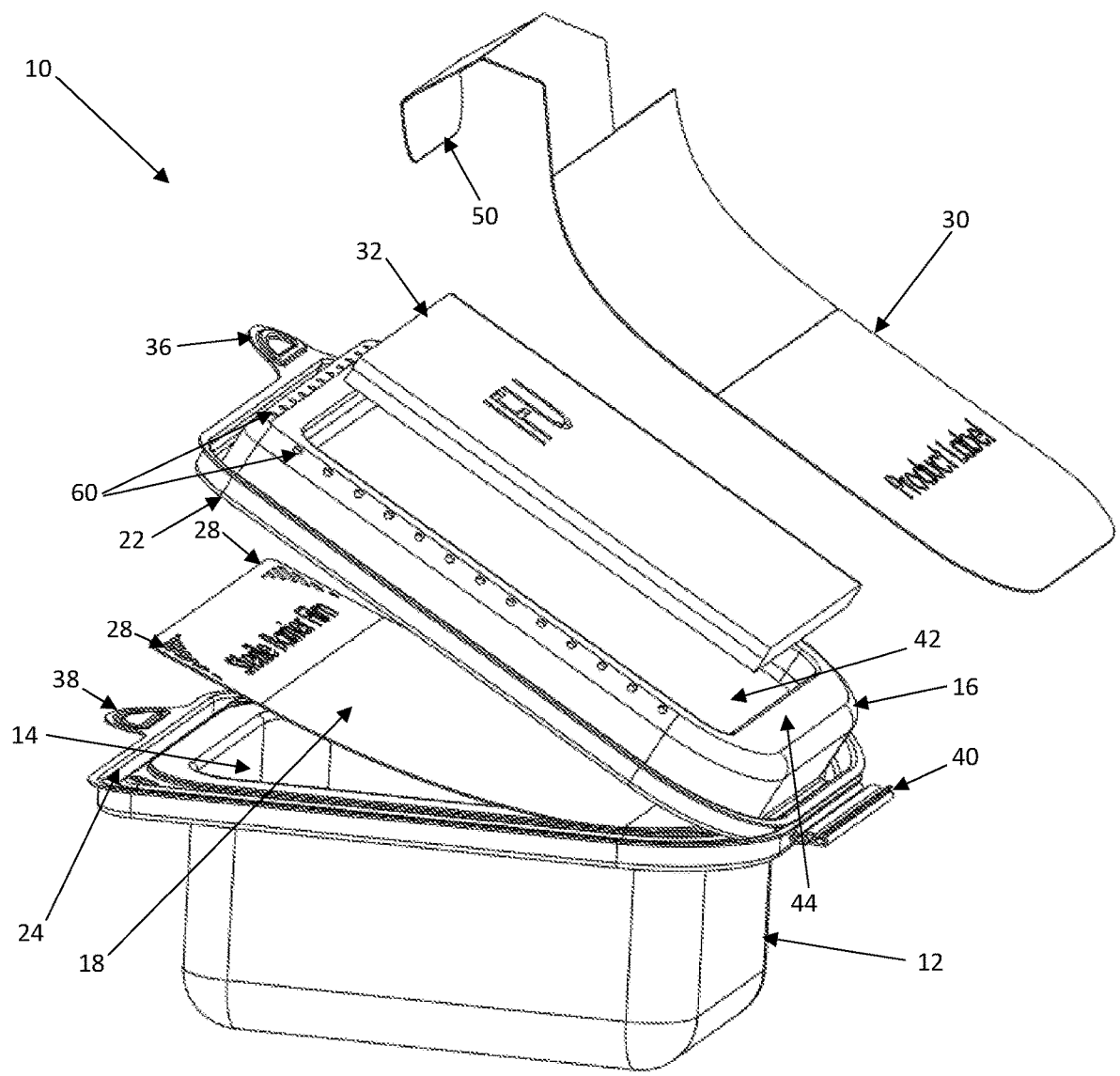
FIG. 1 is an exploded view of a packaging assembly.

Aspects of the disclosure are directed to packaging assemblies for medical devices and components or products. Such packaging assemblies can be terminally sterilized. Because such medical devices and components are often intricate and delicate, packaging that protects the component is desired. Many packaging assembly configurations described in this disclosure support and protect the medical device component during transit and storage, while also providing a significantly smaller footprint than traditional packaging arrangements. Many of the disclosed packaging assemblies are also expected to require less components/materials, reduce inventory and shipping costs, provide a superior sterile barrier, protect the barrier from damage during transportation and handling, manage product information, documentation and/or accessories and also provide visibility as compared to many conventional sterile medical device packages.

Specific details of embodiments of the disclosure are described below with reference to FIGS. 1-8. It will be appreciated that the disclosed embodiments may also be used for a wide variety of types of medical devices and components. Particular examples of medical device components that can be stored or part of the disclosed packaging assemblies include catheter-based delivery system components and perfusion products, however, the disclosure is not intended to be limited to these categories of products.

One packaging assembly 10 is illustrated in FIGS. 1-5. The packaging assembly 10 is particularly suitable for storing terminally sterilized medical device components/products 1. The packaging assembly 10 includes a tray 12 defining a compartment 14, a lid 16 and a removable barrier film 18 that can separate and create a sterile barrier between the lid 16 from the tray 12. The compartment 14 can optionally be configured to correspond to the shape of the medical device 1 to be stored or, alternatively, can include a generic, rectangular or otherwise shaped compartment. Suitable materials for the tray 12 and the lid 16 include, but are not limited to, moldable thermoplastics having a somewhat flexible nature such as high-density polyethylene (HDPE) or polyethylene terephthalate (PETG). Compartments formed to have other shapes are also envisioned. In some embodiments, the tray 12 includes a receiving surface 20 circumscribing the compartment 14, parallel to a plane in which the lid 16 lies, for supporting and receiving the barrier film 18.

Figure 2:
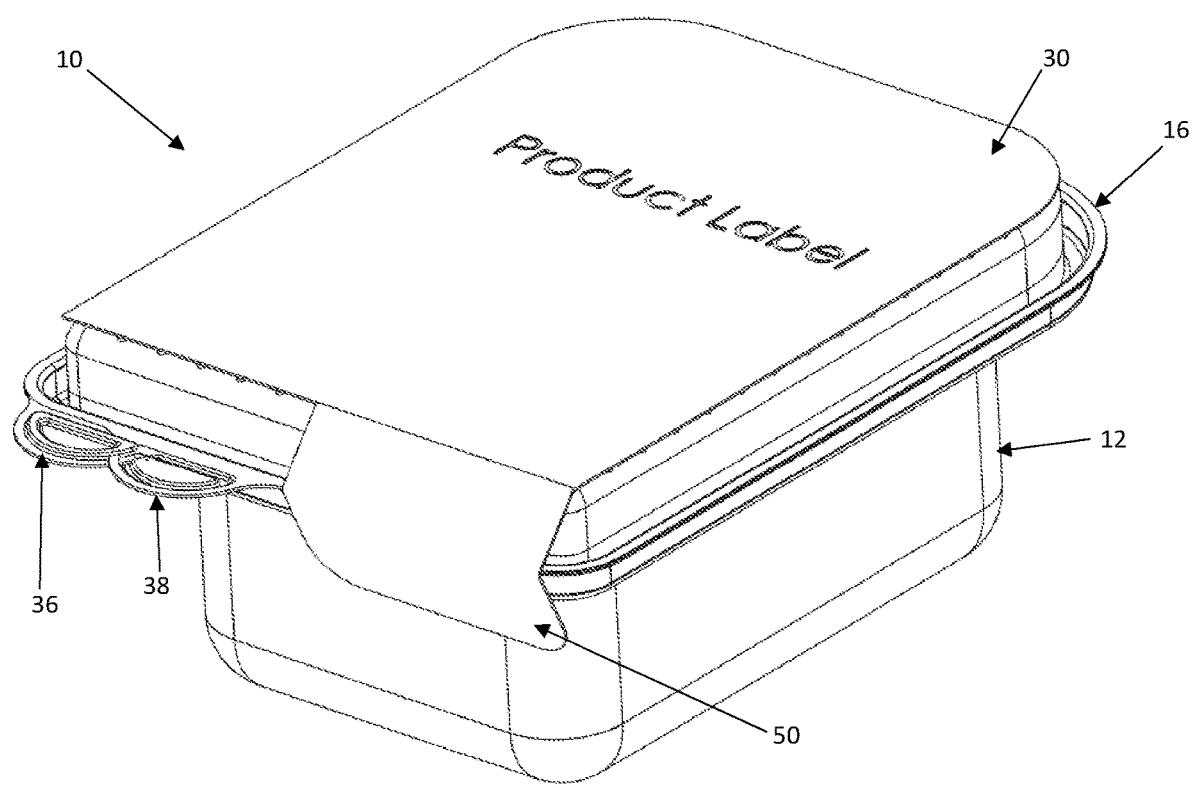
FIG. 2 is a perspective view of the packaging assembly of FIG. 1 in a closed configuration.
Figure 3:
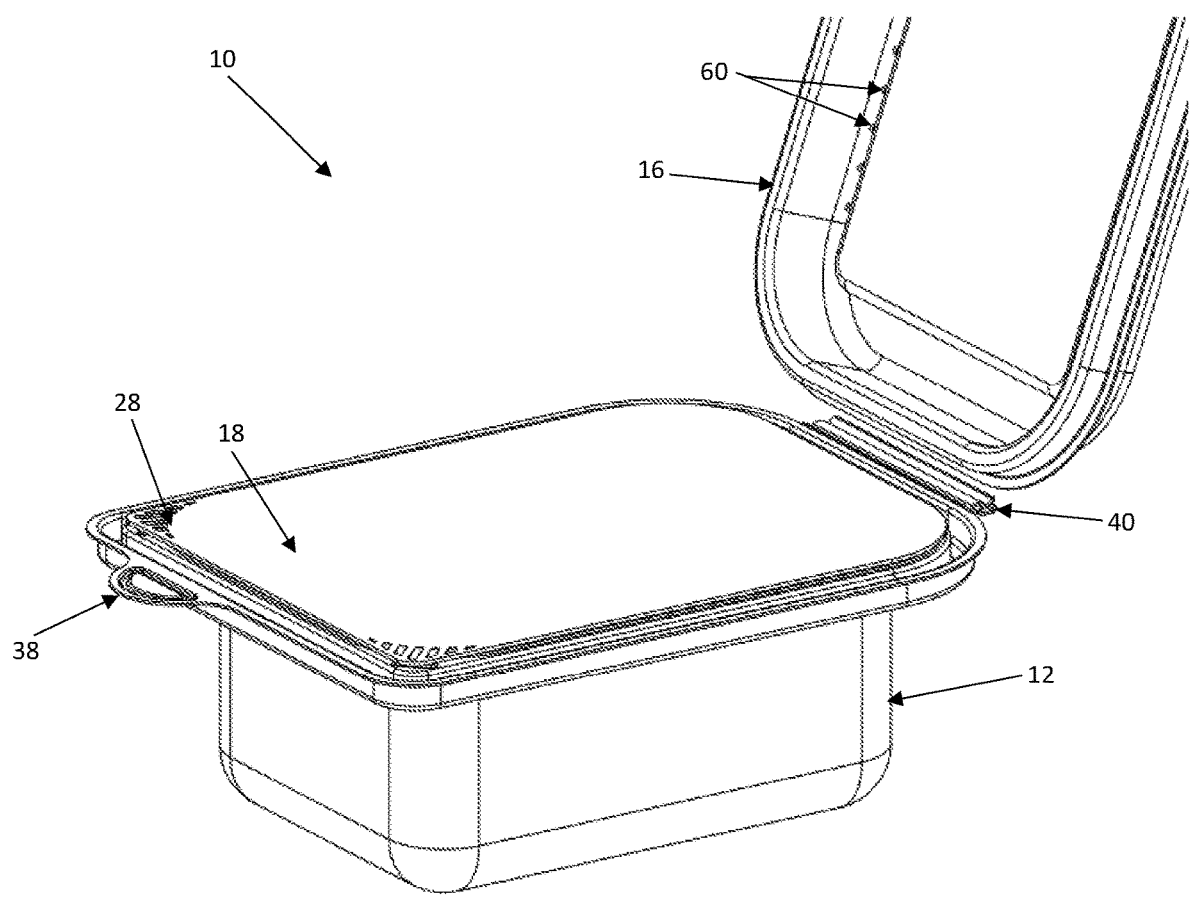
FIG. 3 is a partial, perspective view of the packaging assembly of FIGS. 1-2 in a partially open configuration.
Figure 4:
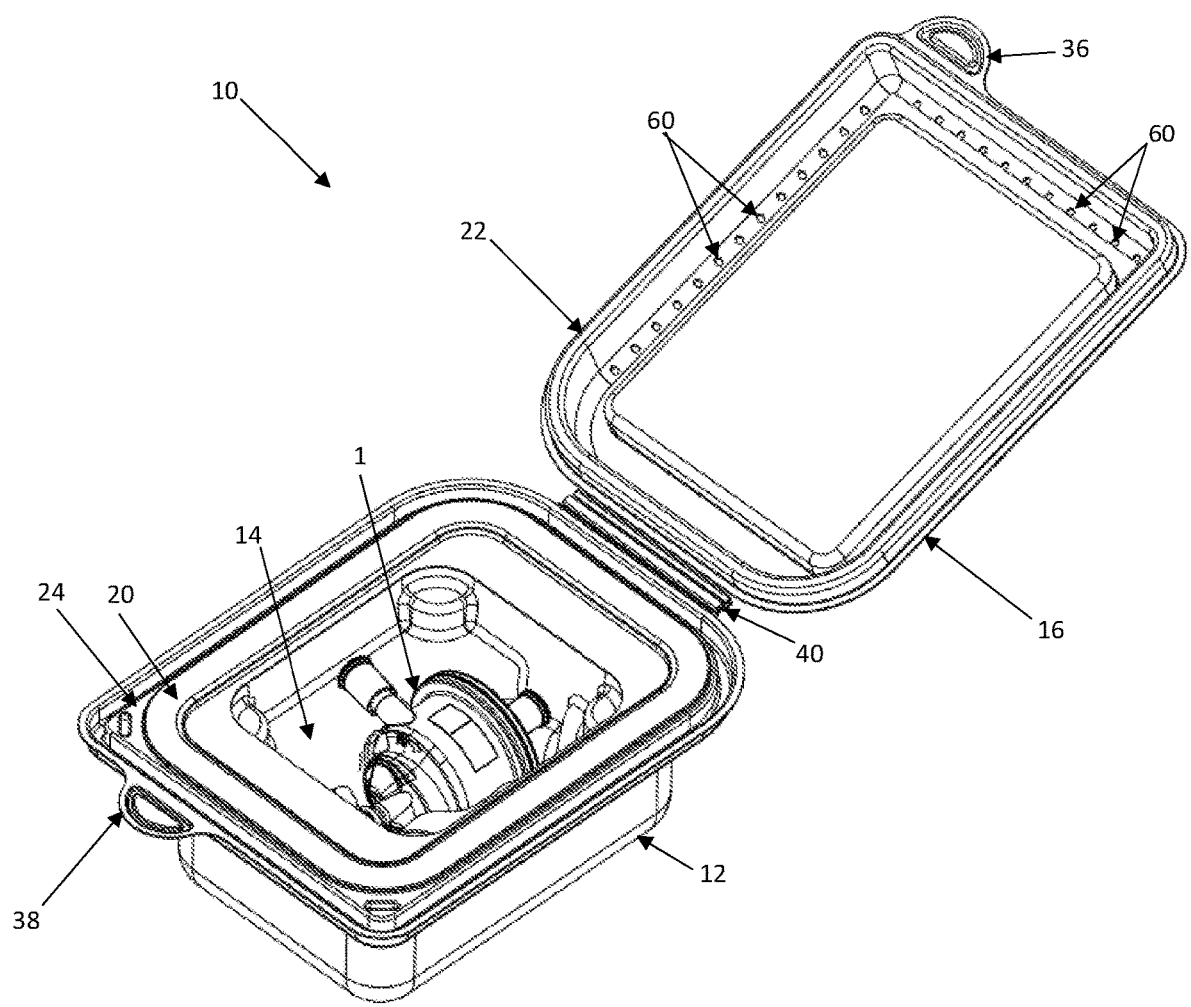
FIG. 4 is a perspective view of the packaging assembly of FIGS. 1-3 in an open configuration.

The barrier film 18 can be made of a permeable film such as Tyvek® (flashspun high-density polyethylene fibers), for example, and provides a moisture and contaminant barrier, while allowing air and also the egress of various gas sterilization techniques such ethylene oxide, for example, to flow past the barrier film 18. The barrier film can also be non-permeable film for use with energy-based sterilization techniques such as e-beam and gamma for example. The barrier film 18 can be secured to the tray 12 via heat melting or the like and can be removed prior to use by peeling away the barrier film 18 from the tray 12. In some embodiments, the barrier film 18 can include one or more tabs 28 supported away from the receiving surface 20 for the user to grip to pull away the barrier film 18 from the receiving surface 20 in order to access a component stored within the compartment 14. As shown, in one embodiment, the barrier film 18 is generally sized to both seal the compartment 14 and be contained within the package assembly 10 when the lid 16 is operatively secured to the tray 12 in the closed configuration (FIG. 2).

When the package assembly 10 is in a closed configuration (FIG. 2), the barrier film 18 seals the compartment and a corresponding lip/groove 22/24 of the lid 16 and tray 12 are engaged. In some embodiments, the lip/groove 22/24 can be configured such that a blade or other sharp object (not shown) cannot practically be inserted between the lid 16 and the tray 12 (see, in particular, FIG. 5) when the packaging assembly is in the closed configuration, thereby lowering the potential for the sterile barrier film being punctured. In the closed configuration, a label 30 is secured over one or more product items or accessories 32 thereby securing the product items 32 to the lid 16 prior to use. In some embodiments, the lid 16 is hingedly connected to the tray 12 with a living hinge 40 or the like. In this way, the lid 16 remains connected to tray 12 after the packaging assembly 10 is in the open configuration (FIG. 4), which is beneficial in embodiments where the lid 16 includes a label 30 to identify the stored component as well as retain instructions for use and/or other product item(s) 32 positioned below the label 30. To enhance the ease in which the lid 16 can be opened with respect to the tray 12, the lid 16 and/or the tray 12 optionally include staggered tabs 36, 38, which provide an area in which a user can grip the lid 16 and/or tray 12 to pry the lip 22 of the lid 16 from the groove 24 of the tray 12.

To provide a compartment for any optional product item(s) 32 relating to the packaged medical device component 1, the lid 16 can include a recess 42 optionally outlined by a receiving surface 44 to support the label 30 above the recess 42 on the lid 16. The product items 32 can include a variety of items associated with the particular medical device component including sheets of product documentation, instructions for use, readable memory storing product software or other files, or other non-sterile accessories, etc. The label 30 can include printed product identifying information and specifications, for example. The label 30 can be sized to cover the recess 42 and, in the closed configuration, the label 30 can positioned on the receiving surface 44 to generally seal the product item(s) 32 within the recess 42. To access the product item(s) 32, the label 30 is peeled back from the receiving surface 44 and recess 42. In some embodiments, the label 30 will include a releasable adhesive to releasably secure the label 30 to the receiving surface 44. The label 30 can also include a tab 50 that extends past the receiving surface 44 and which can provide an area for the user to grip when the label 30 is to be peeled away from the receiving surface 44 to expose the recess 42. The tab 50 can also be configured to tear when the lid 16 is lifted from the tray 12 to provide some indication that the packaging assembly 10 has been previously opened.

Figure 5:
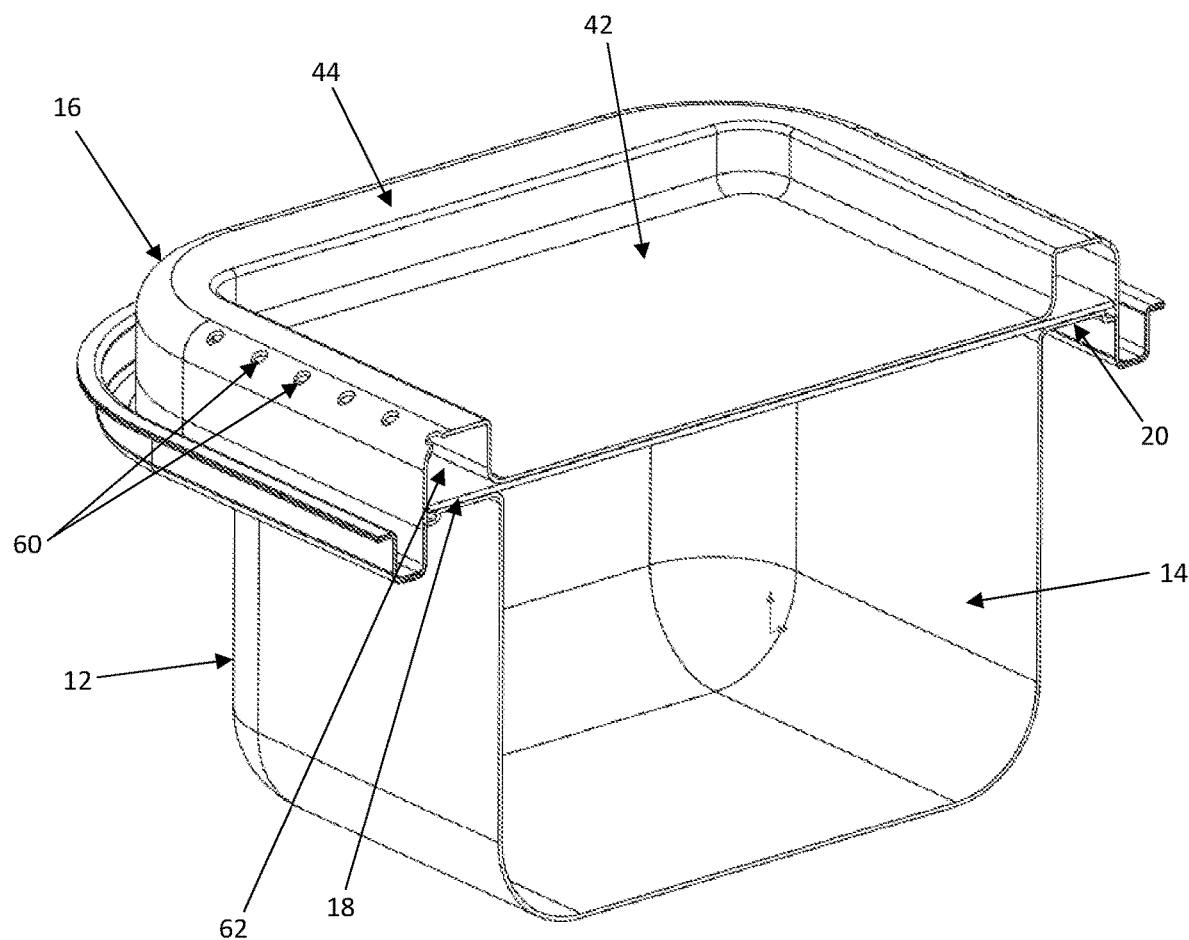
FIG. 5 is a partial, cross-sectional view of the packaging assembly of FIGS. 1-4 having various elements omitted for ease of illustration.

The packaging assembly 10 can also optionally be configured to allow for sterilization of a medical device component stored within the compartment 14. As best shown in FIG. 5, the lid 16 can include one or more vents 60 (only a select few of which are referenced) so that gas or energy beam sterilization techniques can be utilized. In this way, gas can be directed from outside of the packaging assembly through a passageway to the compartment 14 via the vents 60, into a channel 62 formed by the lid 16 and then through the barrier film 18 and into the compartment 14 to subsequently sterilize a device contained therein. In the particular embodiment illustrated, the channel extends around the entire perimeter of the lid 16 and also the receiving surface 20 but this is not required. In one optional embodiment, the lid 16 includes multiple vents 60 spaced along three sides of the lid 16.

The packaging assembly 10 can be sterilized in a variety of other ways. The packaging assembly 10 can be sterilized, via energy beam either with the lid 16 in the open position or after the lid 16 is secured over the tray 12 to cover the tray 12 in embodiments including one or more vents 60. Once the medical device component 1 and compartment 14 are covered by the barrier film 18 and sterilized, other nonsterile items can be incorporated into the packaging assembly 10 (e.g., the lid 16 if not originally provided, the label 30 and/or any product item(s) 32).

Figure 6:
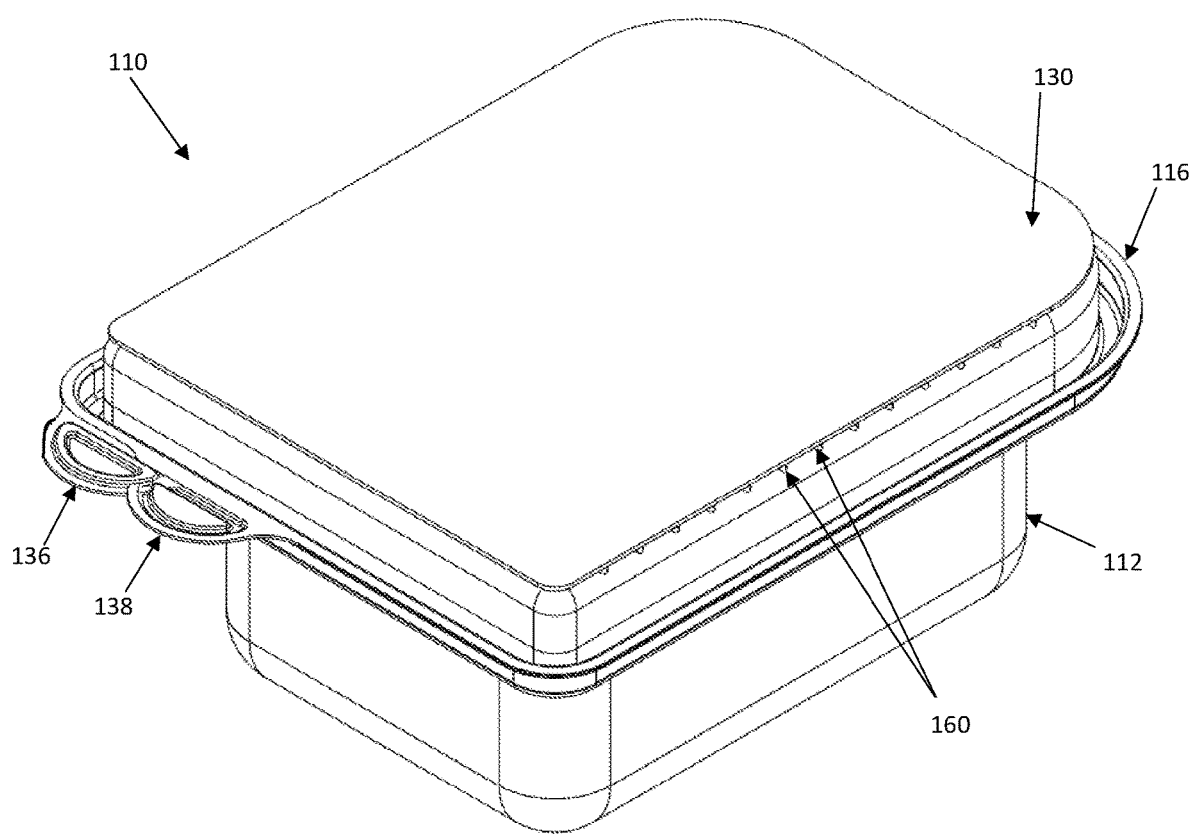
FIG. 6 is a front perspective view of an alternate packaging assembly in a closed configuration.
Figure 7:
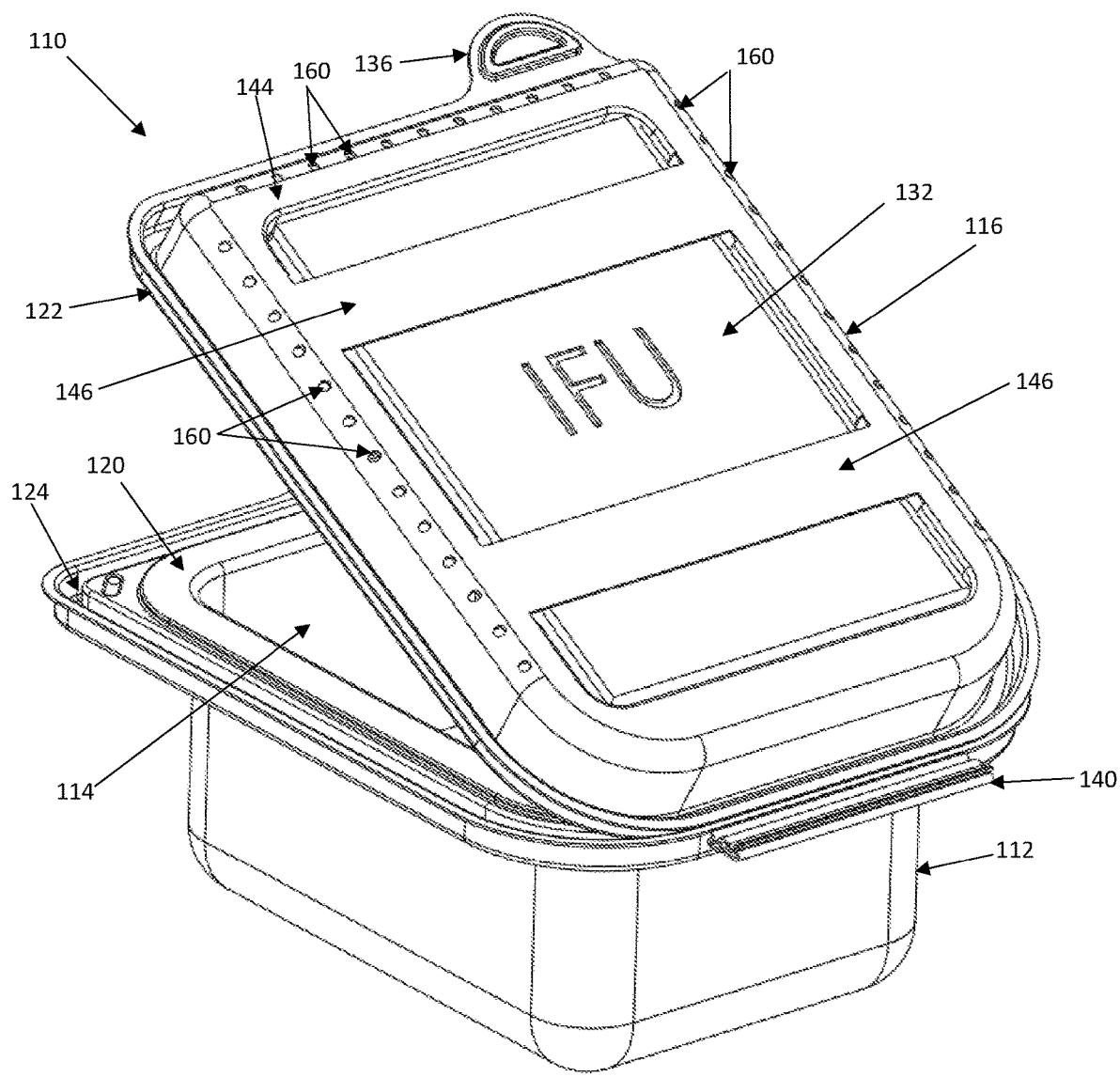
FIG. 7 is a rear perspective view of the packaging assembly of FIG. 6 in an open configuration in which a label has been removed to expose a product item or accessory.
Figure 8:
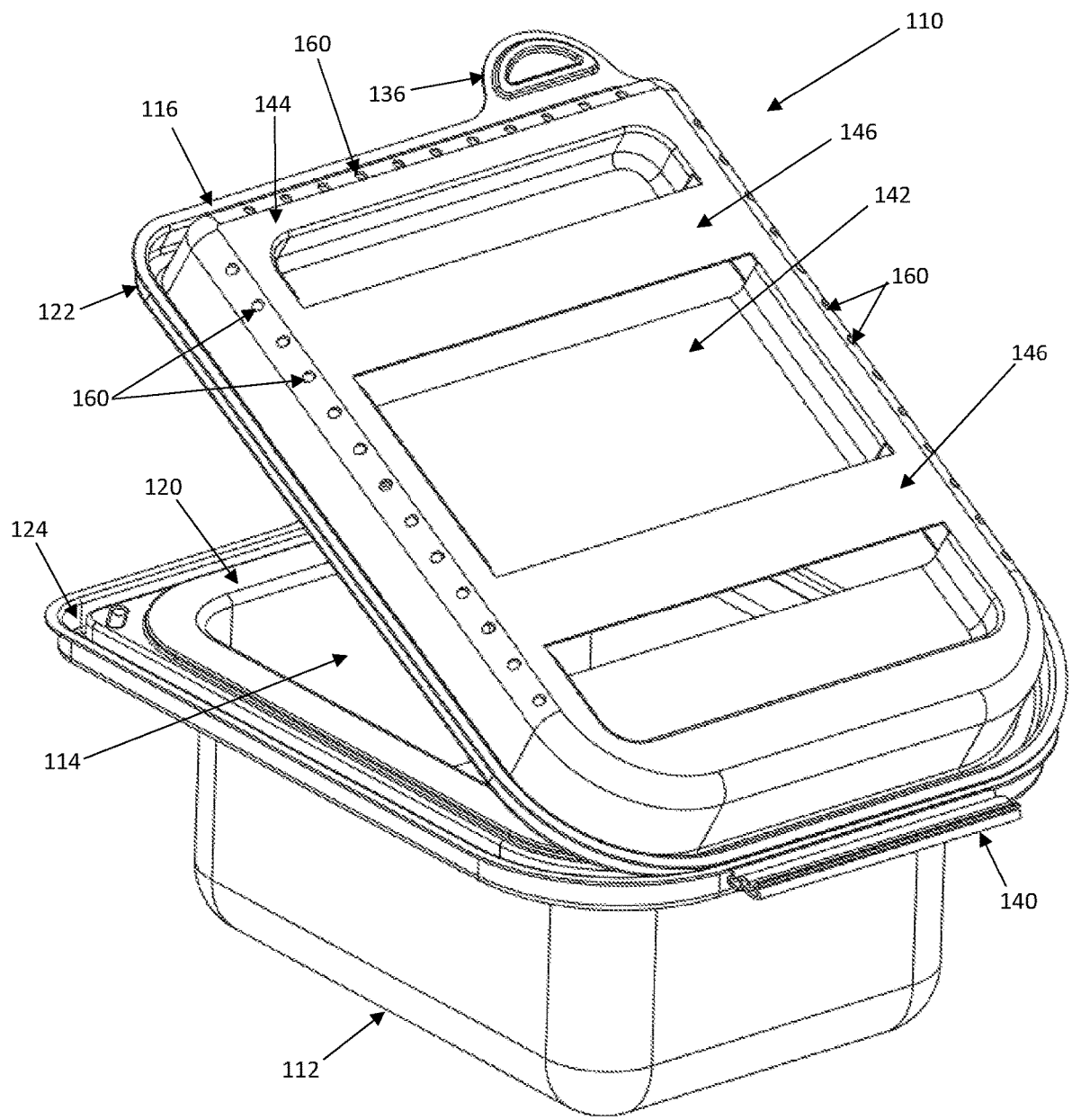
FIG. 8 is a rear perspective view of the packaging assembly of FIG. 6 in an open configuration in which the label and product documentation have been removed.

An additional embodiment of a packaging assembly is illustrated in FIGS. 6-8. This embodiment is largely similar to the packaging assembly of FIGS. 1-5 except as explicitly stated. The packaging assembly 110 is also particularly suitable for storing terminally sterilized medical device components/products (not shown). The packaging assembly 110 includes a tray 112 defining a compartment 114, a lid 116 and a removable barrier film (not shown) that can separate and create a sterile barrier between the lid 116 from the tray 112 (see also FIG. 3 and related disclosure). The compartment 114 can optionally be configured to correspond to the shape of the medical device component or product to be stored. Suitable materials for the tray 112 and the lid 116 include moldable thermoplastics having a somewhat flexible nature such those disclosed above. As with the prior illustrated embodiment, the tray 112 includes a receiving surface 120 circumscribing the compartment 114, parallel to a plane in which the lid 116 lies, for supporting and receiving the barrier film (omitted in FIGS. 6-8 for ease of illustration, however, it will be understood that the barrier film can be identically configured as disclosed with respect to FIGS. 1-5).

When the package assembly 110 is in a closed configuration as is shown in FIG. 6, the barrier film seals the compartment and a corresponding lip/groove 122/124 of the lid 116 and tray 112 are engaged. In some embodiments, the lip/groove 122/124 is configured such that a blade (not shown) cannot practically be inserted between the lid 116 and the tray 112 when the packaging assembly is in the closed configuration. The packaging assembly 110 further includes a label 130, which in the closed configuration is secured over product item(s) 132 thereby securing the product item(s) 132 to the lid 116. In this embodiment, the lid 116 includes a recess 142 circumscribed by a receiving surface 144 to support the label 130 above the recess 142 on the lid 116. The lid 116 further includes one or more straps 146 extending between ends of the receiving surface 144. The straps 146 are positioned so that the product item(s) 132 can be slid into the recess 142 and generally maintained therein until a user pulls the product documentation out of the recess 142.

The label 130 can include printed product identifying information and specifications, for example. In some embodiments, the lid 116 is hingedly connected to the tray 112 with a living hinge 140 or the like. In this way, the lid 116 remains connected to tray 112 after the packaging assembly 110 is in the open configuration, which is beneficial in embodiments where the lid 116 includes the label 130 to identify the stored component as well as retain instructions for use and/or other product item(s) 132 positioned below the label 130 and straps 146. To enhance the ease in which the lid 116 can be opened with respect to the tray 112, the lid 116 and/or the tray 112 optionally include staggered tabs 136, 138.

The packaging assembly 110 can also optionally be configured to allow for sterilization of a device stored within the compartment 114 in many ways outlined above. Identical to that previously described with respect to other embodiments, in some embodiments, the lid 116 can include one or more vents 160 (only a select few of which are referenced) to that gas or energy beam sterilization techniques can be utilized in ways discussed above.

Although the present disclosure has been described with reference to preferred embodiments, workers skilled in the art will recognize that changes can be made in form and detail without departing from the spirit and scope of the present disclosure.

What is claimed is:

1. A packaging assembly comprising:
    a tray including at least one compartment adapted to receive a medical device component;
    a barrier film covering the at least one compartment;
    a lid pivotally attached to the tray; wherein the tray and the lid each include cooperative latching features; wherein the lid includes a receiving surface that defines a recess;
    one or more product items positioned within the recess;
    a first strap extending over the recess; and
    a label removably secured on the receiving surface and the first strap, over the recess and over the one or more product items.

2. The packaging assembly of claim 1, wherein the lid is received within a groove formed in the tray when the package assembly is in a closed configuration.

3. The packaging assembly of claim 1, wherein the barrier film is made of flashspun high-density polyethylene fibers.

4. The packaging assembly of claim 1, wherein the package assembly further includes a product and the tray is molded to confirm conform to the product.

5. The packaging assembly of claim 1, further comprising a feature that indicates whether the package assembly has been opened.

6. The packaging assembly of claim 1, wherein the one or more product items are selected from the group consisting of instructions for use, readable memory, or other non-sterile accessories.

7. The packaging assembly of claim 1, wherein the label includes a tab that interconnects the lid to the tray.

8. The packaging assembly of claim 1, wherein, when the packaging assembly is in a closed configuration, the packaging assembly forms a passageway for the egress of either energy beam sterilization or gas sterilization.

9. The packaging assembly of claim 8, wherein the packaging assembly defines a plurality of vents for the egress of either energy beam sterilization of or gas sterilization.

10. The packaging assembly of claim 9, wherein the lid defines a channel between the vents and the barrier film.

11. The packaging assembly of claim 1, further comprising a medical device component positioned within the tray and wherein the tray is configured to support the medical device component away from the barrier film.

12. The packaging of claim 1, wherein the lid further includes a second strap extending across and supported above the recess.

13. The packaging assembly of claim 1, wherein the barrier film includes a tab that is supported off of the tray.

14. The packaging assembly of claim 1, wherein the one or more product items includes instructions for use of the medical device component.

15. The packaging assembly of claim 10, wherein the channel extends along at least two sides of the recess.

16. The packaging assembly of claim 1, wherein the receiving surface encircles the recess and the label secures the one or more product items to the lid.

* * * * *